US006060316A

United States Patent [19]
Young et al.

[11] Patent Number: 6,060,316
[45] Date of Patent: May 9, 2000

[54] METHODS OF TARGETING OF VIRAL ENTRY

[75] Inventors: John A. T. Young, Newton; Richard C. Mulligan, Lincoln; Sophie Snitkovsky; Thomas M. J. Niederman, both of Brookline, all of Mass.

[73] Assignees: President and Fellows of Harvard College; The Children's Medical Center Corp., both of Boston, Mass.

[21] Appl. No.: 09/327,841

[22] Filed: Jun. 8, 1999

Related U.S. Application Data

[60] Provisional application No. 60/088,622, Jun. 9, 1998.

[51] Int. Cl.$^7$ ............................. C12N 15/85; C12N 15/63
[52] U.S. Cl. ......................................... 435/455; 435/320.1
[58] Field of Search ................................. 435/320.1, 455

[56] References Cited

FOREIGN PATENT DOCUMENTS

| | | | |
|---|---|---|---|
| 2 649 119 | 1/1991 | France | 435/173.1 |
| WO 93/09221 | 5/1993 | WIPO | 435/325 |
| WO 93/25682 | 12/1993 | WIPO | 424/278.1 |
| WO 94/27643 | 12/1994 | WIPO | 514/44 |
| WO 97/11604 | 4/1997 | WIPO | 424/405 |
| WO 97/23608 | 7/1997 | WIPO | 435/455 |
| WO 98/47916 | 10/1998 | WIPO | 435/455 |

OTHER PUBLICATIONS

Snitkovsky S. and Young J.A., "Cell–specific viral targeting mediated by a soluble retroviral receptor–ligand fusion protein," *Proc. Natl. Acad. Sci U.S.A.*, 9512);7063–7068 (Jun. 9, 1998).

Damico, R.L. et al., "Receptor–triggered membrane association of a model retroviral glycoprotein," *Proc. Natl. Acad. Sci. U.S.A.*, 95(5):2580–2585 (Mar. 3, 1998).

Hernandez, L.D. et al., "Activation of a retroviral membrane fusion protein: soluble receptor–induced liposome binding of the ALSV envelope glycoprotein," *J. Cell Biol.*, 139(6):1455–1464 (Dec. 15, 1997).

Etienne–Julan, M. et al., "The efficiency of cell targeting by recombinant retroviruses depends on the nature of the receptor and the composition of the artificial cell–virus linker," *J. of General Virology*, 73:3251–3255 (1992).

Kasahara, N. et al., "Tissue–Specific Targeting of Retroviral Vectors Through Ligand–Receptor Interactions," *Science*, 266:1373–1376 (Nov. 25, 1994).

Kasahara, N. et al., "Tissue–specific targeting of retroviral vectors via ligand–receptor interactions," *Advanced Drug Delivery Reviews*, 17:227–234 (1995).

Han, X. et al., "Ligand–directed retroviral targeting of human breast cancer cells," *Proc. Natl. Acad. Sci. USA*, 92:9747–9751 (Oct. 1995).

Cosset, F.L. and Russell, S.J., "Targeting retrovirus entry," *Gene Therapy*, 3:946–956 (1996).

Chu, T.H.T., and Dornburg, R., "Toward Highly Efficient Cell–Type–Specific Gene Transfer with Retroviral Vectors Displaying Single–Chain Antibodies," *J. of Virology*, 71:720–725 (Jan. 1997).

Valsesia–Wittmann, S. et al., "Modifications in the Binding Domain of Avian Retrovirus Envelope Protein To Redirect the Host Range of Retroviral Vectors," *J. of Virology*, 68:4609–4619 (Jul. 1994).

Somia, N.V., et al., "Generation of targeted retroviral vectors by using single–chain variable fragment: An approach to in vivo gene delivery," *Proc. Natl. Acad. Sci. U.S.A.*, 92:7570–7574 (Aug. 1995).

Roux, P. et al., "A versatile and potentially general approach to the targeting of specific cell types by retroviruses: Application to the infection of human cells by means of major histocompatibiligy complex class I and class II antigens by mouse ecotropic murine leukemia virus–derived viruses," *Proc. Natl. Acad. Sci. U.S.A.*, 86:9079–9083 (Dec. 1989).

Davey, R.A. et al., "In Vitro Binding of Purified Murine Ecotropic Retrovirus Envelope Surface Protein to Its Receptor, MCAT–1," *J. of Virology*, 71:8096–8102 (Nov. 1997).

Matano, T. et al., "Targeted infection of a retrovirus bearing a CD4–Env chimera into human cells expressing human immunodeficiency virus type 1," *J. of General Virology*, 76:3165–3169 (1995).

Cosset, F.L. et al., "Retroviral Retargeting by Envelopes Expressing an N–Terminal Binding Domain," *J. of Virology*, 69:6314–6322 (Oct. 1995).

Ager, S. et al., "Retroviral Display of Antibody Fragments; Interdomain Spacing Strongly Influences Vector Infectivity," *Human Gene Therapy*, 7:2157–2164 (Nov. 10, 1996).

Valsesia–Wittman, S. et al., "Improvement of Retroviral Retargeting by Using Amino Acid Spacers between an Additional Binding Domain and the N Terminus of Moloney Murine Leukemia Virus Su," *J. of Virology*, 70(3):2059–2064 (Mar. 1996).

Marin, M. et al., "Targeted Infection of Human Cells via Major Histocompatibility Complex Class I Molecules by Moloney Murine Leukemia Virus–Derived Viruses Displaying Single–Chain Antibody Fragment–Envelope Fusion Proteins," *J. of Virology*, 70(5):2957–2962 (May 1996).

Neda, H. et al., "Chemical Modification of an Ecotropic Murine Leukemia Virus Results in Redirection of Its Target Cell Specificity," *The Journal of Biological Chemistry*, 266(22):14143–14146 (Aug. 5, 1991).

Nilson, B.H.K. et al., "Targeting of retroviral vectors through protease–substrate interactions," *Gene Therapy*, 3:280–286 (1996).

Chu, T.H.T. et al., "Cell targeting with retroviral vector particles containing antibody–envelope fusion proteins," *Gene Therapy*, 1:292–299 (1994).

Martin, F. et al., "Retroviral Vector Targeting to Melanoma Cells by Single–Chain Antibody Incorporation in Envelope," *Human Gene Therapy*, 9:737–746 (Mar. 20, 1998).

(List continued on next page.)

*Primary Examiner*—John S. Brusca
*Assistant Examiner*—William Sandals
*Attorney, Agent, or Firm*—Hamilton, Brook, Smith & Reynolds, P.C.

[57] ABSTRACT

Novel targeting methods of viral entry are disclosed herein.

28 Claims, 1 Drawing Sheet

OTHER PUBLICATIONS

Valsesia–Wittmann, S. et al., "Receptor co–operation in retrovirus entry: recruitment of an auxiliary entry mechanism after retargeted binding," *The EMBO Journal*, 16(6):1214–1223 (1997).

Fielding, A.K. et al., "Inverse Targeting of Retroviral Vectors: Selective Gene Transfer in a Mixed Population of Hematopoietic and Nonhematopoietic Cells," *Blood*, 91(5):1802–1809 (Mar. 1, 1998).

Chu, T.H.T. and Dornburg, Ralph, "Retroviral Vector Particles Displaying the Antigen–Binding Site of an Antibody Enable Cell–Type–Specific Gene Transfer," *J. of Virology*, 69(4):2659–2663 (Apr. 1995).

Michael, S.I. et al., "Strategies to Accomplish Targeted Gene Delivery Employing Tropism–Modified Recombinant Adenoviral Vectors," *Cancer Gene Therapy*, 2(4):321 (1995), Abstract O–44.

Nilson, B.H.K. et al., "Regulatable Tropism of Retroviral Vectors Displaying a Cleavable Polypeptide Ligand," *Cancer Gene Therapy*, 2(4):322–323 (1995), Abstract O–51.

Porter, C.D. et al., "Comparison of Efficiency of Infection of Human Gene Therapy Target Cells via Four Different Retroviral Receptors," *Human Gene Therapy*, 7:913–919 (May 20, 1996).

Peng, K.W. et al., "A Gene Delivery System Activatable by Disease–Associated Matrix Metalloproteinases," *Human Gene Therapy*, 8:729–738 (Apr. 10, 1997).

Goud, B. et al., "Antibody–Mediated Binding of a Murine Ecotropic Moloney Retroviral Vector to Human Cells Allows Internalization But Not the Establishment of the Proviral State," *Virology*, 163:251–254 (1988).

Russell, S.J. et al., "Retroviral vectors displaying functional antibody fragments," *Nucleic Acids Research*, 21(5):1081–1085 (1993).

Schnell, M.J. et al., "Foreign glycoproteins expressed from recombinant vesicular stomatitis viruses ae incorporated efficiently into virus particles," *Proc. Natl. Acad. Sci. U.S.A.*, 93:11359–11365 (Oct. 1996).

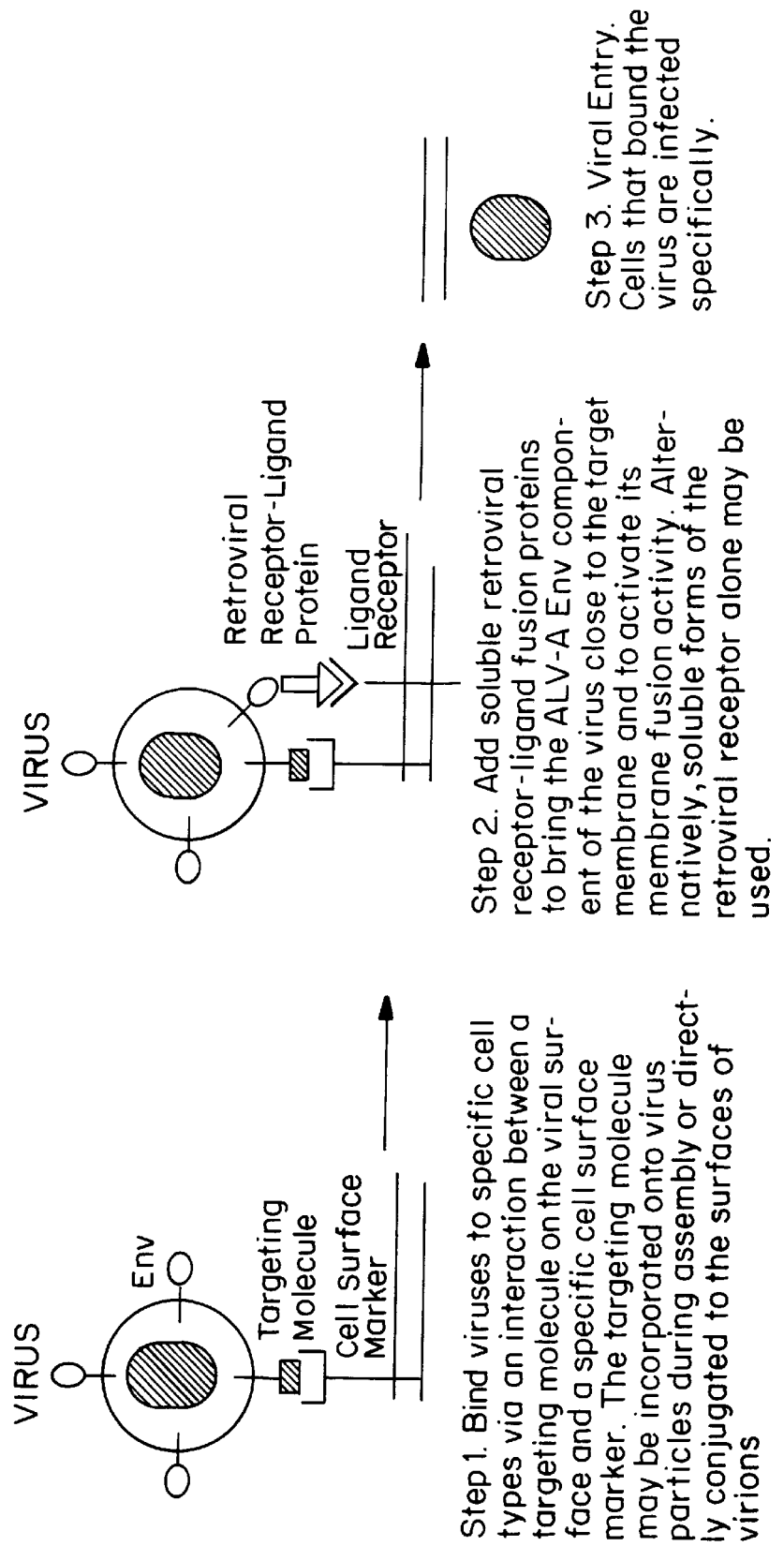

METHODS OF TARGETING OF VIRAL ENTRY

RELATED APPLICATION

This application claims priority to U.S. Provisional Application No. 60/088,622, filed Jun. 9, 1998, the contents of which are incorporated herein by reference in their entirety.

GOVERNMENT SUPPORT

The invention described herein was supported in whole or in part by Grant No. CA6200 from the National Institutes of Health. The United States government has certain rights in the invention.

BACKGROUND OF THE INVENTION

The normal mechanism of viral entry requires interactions between viral envelope proteins and cellular receptors and, in some cases, also cellular co-receptors. Such a mechanism presents limitations in the ability to target viral vectors to specific cell types. For example, such a mechanism makes it difficult to target viral vectors of interest to cell types lacking cellular receptors which interact with viral envelope proteins of the viral vectors of interest.

Thus, there is a continued need to develop new and improved methods for targeting viral vectors to specific cell types.

SUMMARY OF THE INVENTION

The present invention relates to novel targeting methods of viral entry. In these methods, a virus (viral vector) can be targeted to specific cell-types by contacting cells with a virus (viral vector) that possesses on the viral surface a targeting molecule which binds to a surface protein on a target cell. The virus (viral vector) binds to the target cell via an interaction between the targeting molecule on the viral surface and a specific cell surface marker. The targeting molecule can be incorporated onto virus particles during viral assembly. Alternatively, the targeting molecule can be directly conjugated to the surfaces of virions.

To activate or otherwise induce steps for viral entry and thus, infection, a soluble viral receptor-ligand fusion molecule is added, either subsequently or simultaneously. The soluble viral receptor moiety of the soluble viral receptor-ligand fusion molecule binds to a specified viral target on the virus (viral vector), generally a surface protein of the viral particle. Interaction with or binding of the soluble viral receptor to the specified viral target activates or otherwise induces steps for viral entry and, thus, infection. In a preferred embodiment, the viral surface protein is generally a viral protein which binds to a native extracellular domain of a viral cellular receptor, such as a viral cellular receptor on the target cell, and activates or otherwise induces steps for viral entry and, thus, infection. The ligand moiety of the fusion molecule binds to a cell-type specific cellular receptor. In a particular embodiment, soluble forms of the viral receptor alone can be added instead of a soluble viral receptor-ligand fusion molecule. Viral entry occurs in cells bound by the virus (viral vector).

In a particular embodiment, the present invention relates to a targeting method of retroviral entry. In this method a retrovirus (retroviral vector) can be targeted to specific cell-types by contacting cells with a retrovirus (retroviral vector) that possesses on the viral surface a targeting molecule which binds to a surface protein on a target cell. The virus (vector) binds to the target cell via an interaction between the targeting molecule on the viral surface and a specific cell surface marker. The targeting molecule can be incorporated onto virus particles during viral assembly. Alternatively, the targeting molecule can be directly conjugated to the surfaces of virions. To bring the envelope component of the retrovirus (retrovirus vector) sufficiently close to the membrane of the target cell and to activate its membrane fusion activity, or otherwise induce steps for retroviral entry and thus, infection, a soluble retroviral receptor-ligand fusion molecule is added, either subsequently or simultaneously. The soluble retroviral receptor moiety of the soluble retroviral receptor-ligand fusion molecule binds to the envelope component of the virus (viral vector). Interaction with or binding of the retroviral receptor moiety to the viral envelope component activates or otherwise induces steps for viral entry and, thus, infection. The ligand moiety of the fusion molecule binds to a cell-type specific cellular receptor. In a particular embodiment, soluble forms of the retroviral receptor alone can be added instead of a soluble viral receptor-ligand fusion molecule. Viral entry occurs in cells bound by the virus (retroviral vector).

BRIEF DESCRIPTION OF THE DRAWING

The FIGURE is a schematic diagram of the novel targeting method of retroviral entry described herein.

DETAILED DESCRIPTION OF THE INVENTION

The present invention relates to novel targeting methods of viral entry. In these methods, a virus (viral vector) can be targeted to specific cell-types by contacting cells with a virus (viral vector) that possesses on the viral surface a targeting molecule which binds to a surface protein on a target cell. The virus can include in its genome a nucleic acid sequence encoding a desired protein. The virus (viral vector) binds to the target cell via an interaction between the targeting molecule on the viral surface and a specific cell surface marker. The targeting molecule can be incorporated onto virus particles during viral assembly. Alternatively, the targeting molecule can be directly conjugated to the surfaces of virions. The targeting molecule is engineered using known methods in the course of manufacturing a viral vector.

Viral vectors include retrovirus, adenovirus, parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include, for example, Norwalk viruses, togaviruses, flaviviruses, reoviruses, papovaviruses, hepadnaviruses, and hepatitis viruses. Examples of retroviruses include avian leukosis-sarcoma viruses (e.g., avian leukosis viruses, avian sarcoma viruses), mammalian C-type, B-type, D-type retroviruses, HTLV-BLV viruses, lentiviruses, spumaviruses (Coffin, J. M., "Retroviridae: The viruses and their replication", in *Fundamental Virology*, Third Edition, edited by B. N. Fields, D. M. Knipe, P. M. Howley, et al. Lippincott-Raven Philadelphia, Pa. (1996)). Other examples include murine leukemia viruses, murine sarcoma viruses, mouse mammary tumor viruses, bovine leukemia viruses, feline leukemia viruses, feline sarcoma viruses, avian leukemia viruses, human T-cell leukemia viruses, baboon endogenous viruses, Gibbon ape leukemia viruses, Mason Pfizer monkey viruses, simian immunodeficiency viruses, simian sarcoma viruses, Rous sarcoma viruses and lentiviruses.

Retroviruses are a family of RNA viruses which infect cells in a two step mechanism. These viruses contain two envelope glycoprotein subunits designated surface (SU) and transmembrane (TM) which form an oligomeric complex on the viral surface and mediate viral entry. The SU protein contains the viral receptor binding determinants whereas the TM protein contains a hydrophobic transmembrane region and a separate hydrophobic segment that mediates virus-cell membrane fusion (Weiss, R. A., "Cellular receptors and viral glycoproteins involved in retrovirus entry," pp. 1–107, in J. A. Levy (ed.), *The Retroviridae,* Vol. 2., Plenum Press: New York, N.Y. (1993)). The first step of infection is the binding of the viral particle via the surface protein of the retrovirus envelope (env) protein and viral and cellular membrane fusion for viral uptake via the transmembrane protein of the env protein. The env protein is largely responsible for the specificity (between cell-types and between species) of the infectivity of retroviral vectors.

Adenoviruses have a linear double-stranded DNA genome. Adenoviruses infect cells by a two step mechanism. First a viral surface fiber protein binds specifically to a cell surface receptor. In the case of human HeLa cells, the receptor for adenoviruses 2 and 5 is designated CAR, a member of the immunoglobulin protein superfamily, which also serves as a cellular receptor for coxsackie B viruses (Bergelson, *Science,* 275:1320–1323 (1996)). However, other viral receptors have been described. Following receptor binding, adenoviruses are taken up into the cell by receptor-mediated endocytosis and interaction between the viral penton base protein and cellular integrins is necessary for viral entry (Wickham, *Cell,* 73:309 (1993); Bai, *J. Virol.,* 68:5925 (1994); Goldman, *J. Virol.,* 69:5951 (1995); and Huang, *J. Virol.,* 70:4502 (1996)). The viral DNA is replicated in the cell extrachromosomally (Horwitz, M. S., "Adenoviruses," in *Fields Virology,* Third Edition, edited by B. N. Fields, D. M. Knipe, P. M. Howley et al., Lippincott-Raven Publishers: Philadelphia, Pa. (1996)).

Recombinant adenoviral vectors are generated by a variety of techniques that include introducing a desired gene of interest into a bacterial plasmid at a site flanked by adenovirus sequences. These sequences provide control elements for gene expression and serve as sites for recombination with a compatible adenoviral genome when cotransfected together into an appropriate mammalian cell line (Horwitz, M. S., "Adenoviruses," in *Fields Virology,* Third Edition, edited by B. N. Fields, D. M. Knipe, P. M. Howley et al., Lippincott-Raven Publishers: Philadelphia, Pa. (1996)).

Adeno-associated viruses (AAV) have a linear single-stranded DNA genome and their receptor has not yet been described. These viruses only undergo productive infection if the infected cells are coinfected with a helper virus (e.g., adeno- or herpesvirus) otherwise the genome becomes integrated in a latent state at a specific site on a human chromosome (Linden, *Proc. Natl. Acad. Sci. USA,* 93:11288–11294 (1996); and Berns, K. J., "Parvoviridae: The viruses and their replication" in *Fields Virology,* Third Edition, edited by B. N. Fields, D. M. Knipe, P. M. Howley et al., Lippincott-Raven Publishers: Philadelphia, Pa. (1996)). Recombinant adeno-associated viruses are typically made by replacing viral genes with desired genes of interest or by simply adding the terminal AAV DNA sequences (ITRs) to these genes.

The negative strand RNA viruses infect cells by a variety of different mechanisms. For example, Influenza A viruses which have a segmented RNA genome, contain a surface hemagglutinin protein which binds to cell surface sialic acid receptors and mediates viral entry in a low pH endosome following receptor-mediated endocytosis (Lamb, R. A. and Krug, R. M., "Orthomyxoviridae: The viruses and their replication" *Fields Virology,* Third Edition, edited by B. N. Fields, D. M. Knipe, P. M. Howley et al., Lippincott-Raven Publishers: Philadelphia, Pa. (1996)).

Paramyxoviruses which have a non-segmented RNA genome have two surface viral proteins, the hemagglutinin (HN) and fusion protein (F), required for viral entry which occurs at neutral pH. These viruses can utilize sialic acid receptors, or protein receptors (e.g., CD46 used by measles virus), for viral entry (Lamb, R. A. and Kolakofsky, D., "Paramyxoviridae: The viruses and their replication" *Fields Virology,* Third Edition, edited by B. N. Fields, D. M. Knipe, P. M. Howley et al., Lippincott-Raven Publishers: Philadelphia, Pa. (1996)).

Rhabdoviruses (e.g., VSV) which have a non-segmented RNA genome, contain a surface protein (G) which binds to specific cell surface receptors and mediates viral entry in a low pH endosome. A specific phospholipid appears to be one of the receptors for VSV (Wagner, R. R. and Rose, J. K., in *Fields Virology,* Third Edition, edited by B. N. Fields, D. M. Knipe, P. M. Howley et al., Lippincott-Raven Publishers: Philadelphia, Pa. (1996)).

A number of strategies are currently available for engineering negative strand viral RNA genomes to express heterologous genes (reviewed by Palese, P., *Proc. Natl. Acad. Sci. USA,* 93:11354–11358 (1996); and Schnell, M. J., *Proc. Natl. Acad Sci. USA,* 93:11359–11365 (1996)).

The positive strand RNA viruses also infect cells by a variety of different mechanisms. For example, among the picornaviruses, different members of the immunoglobulin protein superfamily are used as cellular receptors by poliovirus, by the major subgroups of rhinoviruses, and by coxsackie B viruses, whereas an integrin protein is used by some types of ecoviruses and a low density lipoprotein receptor is used by minor subgroups of rhinoviruses (Bergelson, *Science,* 275:1320–1323 (1996); and Rueckert, R. R., "Picomaviridae: The viruses and their replication" Fields Virology, Third Edition, edited by B. N. Fields, D. M. Knipe, P. M. Howley et al., Lippincott-Raven Publishers: Philadelphia, Pa. (1996)). Following receptor-binding, it is not yet known precisely what role receptor-mediated endocytosis plays for picornaviral entry, if indeed it is required.

Because the picornaviruses lack a surface lipid bilayer, their entry pathway does not involve fusion of a viral membrane with a host cell membrane. In contrast, the alphaviruses (e.g., Sindbis virus and Semliki virus) do contain a surface lipid bilayer. These viruses contain two (E1 and E2) surface proteins, and in some cases a third (E3) surface protein important for viral entry. These viruses use various cell surface receptors. For example, Sindbis virus can use a laminin receptor or other receptors and generally enter cells by a pH-dependent mechanism, following receptor-mediated endocytosis (Frolov, *Proc. Natl. Acad. Sci. USA,* 93:11371–11377 (1996); and Schlesinger, S. and Schlesinger, M. J., "Togaviridae: The viruses and their replication," in *Fields Virology,* Third Edition, edited by B. N. Fields, D. M. Knipe, P. M. Howley et al., Lippincott-Raven Publishers: Philadelphia, Pa. (1996)).

The herpesviruses which have large double-stranded DNA genomes, contain a number of surface glycoproteins involved in viral entry and utilize various cell surface receptors. For example, herpes simplex virus and cytomegalovirus entry involves binding to a heparin sulfate cell surface receptor and herpes simplex viruses use other proteins (e.g., HVEM) for viral entry (Montgomery, R., *Cell* 87:427–436 (1996)). In contrast, Epstein-Barr virus entry is initiated by binding to a completely distinct cell surface receptor, CR2 (Wolf, *Intervirology* 35:26–39 (1993)). Strategies have been described that allow one to engineer herpes simplex viruses, cytomegaloviruses and Epstein-Barr viruses as vectors for heterologous gene expression (Roizman, *Proc. Natl. Acad. Sci. USA*, 93:11307–11312 (1996); Andreansky, *Proc. Natl. Acad. Sci. USA*, 93:11313–11318 (1996); Marconi, *Proc. Natl. Acad. Sci. USA*, 93:11319–11320 (1996); Mocarski, *Proc. Natl. Acad. Sci. USA*, 93:11321–11326 (1996); Robertson, *Proc. Natl. Acad. Sci. USA*, 93:11334–11340 (1996); and Duboise, *Proc. Natl. Acad. Sci. USA*, 93:11389–11394 (1996)).

Poxviruses have large double stranded DNA genomes and enter cells by a pH-independent mechanism via receptors that remain to be defined (Moss, B., "Poxviridae: The viruses and their replication," in *Fields virology*, Third Edition, edited by B. N. Fields, D. M. Knipe, P. M. Howley et al., Lippincott-Raven Publishers: Philadelphia, Pa. (1996)). Poxvirus vectors have been used extensively for the expression of heterologous recombinant genes and as vaccines (Moss, B., *Proc. Natl. Acad. Sci. USA*, 93:11341–11348 (1996); and Paoletti, *Proc. Natl. Acad. Sci. USA*, 93:11349–11353 (1996)).

A pseudotyped virus has the env protein from a first retrovirus of a desired specificity and core or structural proteins from a second virus (e.g. a second retrovirus, an orthomyxovirus or a rhabdovirus). Viral pseudotypes have been described, for example, in Le Guen, *Proc. Natl. Acad. Sci. USA*, 89:363–367 (1992); Rizvi, *Journal of Medical Primatology*, 21:69–73 (1992); Takeuchi, *Virology*, 186:792–294 (1992); Vile et al., *Virology*, 180:420 (1991); Miller et al., *J. Virol.*, 65:2220 (1991); Landau, et al.,, *J. Virol.*, 65:162 (1991); Emi, et al., *J. Virol.* 65:1207 (1991); and Dong, et al., *J. Virol.*, 66:7374 (1992). A pseudotyped virus can be targeted to specific cell-types for viral entry in accordance with the present invention.

Typically, retroviral vectors are manufactured by "packaged cell lines" which provide the retroviral proteins necessary for infection (e.g., env, gag and pol), but are incapable of replication upon infection. See, for example, Miller, AD, *Current Topics in Microbiology and Immunology*, Vol. 158, pp. 1–24 (1992).

The viral vectors employed in the present invention can be used for polynucleotide or gene delivery to a cell or animal. The polynucleotide to be delivered to the cell or animal can include a polynucleotide native to the viral vector or heterologous to the vector. Generally, the polynucleotide is present or has been incorporated into the genome of the viral vector. In a preferred embodiment, the viral vector has been engineered to contain a polynucleotide which is itself therapeutic agent or encodes a heterologous therapeutic protein. An example of a therapeutic polynucleotide includes RNA (e.g., ribozymes) and antisense DNA that prevents or interferes with the expression of an undesired protein in the target cell. Examples of therapeutic proteins include antigens or immunogens such as a polyvalent vaccine, cytokines, tumor necrosis factor, interferons, interleukins, adenosine deaminase, insulin, T-cell receptors, soluble CD4, epidermal growth factor, human growth factor, blood factors, such as Factor VIII, Factor IX, cytochrome b, glucocerebrosidase, ApoE, ApoC, ApoAI, the LDL receptor, negative selection markers or "suicide proteins", such as thymidine kinase (including the HSV, CMV, VZV TK), anti-angiogenic factors, Fc receptors, plasminogen activators, such as t-PA, u-PA and streptokinase, dopamine, MHC, tumor suppressor genes such as p53 and Rb, monoclonal antibodies or antigen binding fragments thereof, drug resistance genes, ion channels, such as a calcium channel or a potassium channel, and adrenergic receptors, etc.

In another embodiment, the viral vector has been engineered to contain a polypeptide which encodes a targeting molecule.

As set forth above, the targeting molecule on the viral surface binds to a surface protein on the target cell. A target cell is defined herein as a cell which is intended to be infected by the virus possessing the target molecule on its viral surface. Typically, the target cell is of animal origin and can be a stem cell or somatic cell. Suitable animal cells can be of, for example, mammalian or avian origin. Examples of mammalian cells include human, bovine, ovine, porcine, murine, rabbit cells. The cell may be an embryonic cell, bone marrow stem cell or other progenitor cell. Where the cell is a somatic cell, the cell can be, for example, an epithelial cell, fibroblast, smooth muscle cell, blood cell (including a hematopoietic cell, red blood cell, T-cell, B-cell, etc.), tumor cell, cardiac muscle cell, macrophage, dendritic cell, neuronal cell (e.g., a glial cell or astrocyte), or pathogen-infected cell (e.g., those infected by bacteria, viruses, virusoids, parasites, or prions).

Typically, cells isolated from a specific tissue (such as epithelium, fibroblast or hematopoietic cells) are categorized as a "cell-type." The cells can be obtained commercially or from a depository or obtained directly from an animal, such as by biopsy. Alternatively, the cell need not be isolated at all from the animal where, for example, it is desirable to deliver the virus to the animal in gene therapy.

Cells are typically characterized by markers expressed at their surface that are termed "surface markers". These surface markers include surface proteins, such as cellular receptors, adhesion molecules, transporter proteins, components of the extracellular matrix and the like. These markers, proteins and molecules also include specific carbohydrates and/or lipid moieties, for example, conjugated to proteins. The target molecule on the viral surface binds to one or more surface proteins on the target cell. Surface proteins can be tissue- or cell-type specific (e.g. as in surface markers) or can be found on the surface of many cells. Typically, the surface marker, protein or molecule is a transmembrane protein with one or more domains which extend to the exterior of the cell (e.g. the extracellular domain). Where cell-type specific delivery is desired (as in in vivo delivery of a viral vector), the surface protein selected for the invention is preferably specific to the tissue. By "specific" to the tissue, it is meant that the protein be present on the targeted cell-type but not present (or present at a significantly lower concentration) on a substantial number of other cell-types. While it can be desirable, and even preferred, to select a surface protein which is unique to the target cell, it is not required for the claimed invention. For example, where the cell or cells are contacted with a virus in pure or substantially pure form, such as can be the case in an in vitro gene transfer, specific delivery may not be required. Thus, the surface protein may be present on many different cell-types, specific or even unique to the targeted cell-type.

As set forth above, the surface protein can be a cellular receptor or other protein, preferably a cellular receptor. Examples of cellular receptors include receptors for cytokines, growth factors, and include, in particular epidermal growth factor receptors, platelet derived growth factor receptors, vascular endothelial growth factor receptors (Flk receptors), interferon receptors, insulin receptors, proteins with seven transmembrane domains including chemokine receptors and frizzled related proteins (Wnt receptors), immunoglobulin-related proteins including MHC proteins, CD4, CD8, ICAM-1, etc., tumor necrosis factor-related proteins including the type I and type II TNF receptors, Fas, DR3, DR4, CAR1, etc., low density lipoprotein receptor, integrins, and, in some instances, the Fc receptor.

Other examples of surface proteins include cell-bound tumor antigens. Many of these surface proteins are commercially available and/or have been characterized in the art, including the amino acid and nucleic acid sequences, which can be obtained from, for example, GENBANK, as well as the specific binding characteristics and domains. Cytokine and chemokine receptors are reviewed for example, in Miyama et al., *Ann. Rev. Immunol.,* 10:295–331 (1992); Murphy, *Ann. Rev. Immunol.,* 12:593–633 (1994); and Miller et al., *Critical Reviews in Immunol.,* 12:17–46 (1992).

As set forth above, to activate or otherwise induce steps for viral entry and thus, infection, a soluble viral receptor-ligand fusion molecule can be added, either subsequent to or simultaneously with, contact of cells with a virus (viral vector) that possesses on the viral surface a targeting molecule which binds to a surface protein on a target cell. In a particular embodiment, soluble forms of the viral receptor alone can be added instead of a soluble viral receptor-ligand fusion molecule.

As set forth above, the ligand moiety of the soluble viral receptor-ligand fusion protein binds to a cell-type specific cellular receptor. Typically, the ligand moiety is selected or derived from native ligands or binding partners to the surface protein of the target cell. In the case of a cellular receptor, for example, for a cytokine or growth factor, the ligand moiety can be a polypeptide comprising at least the receptor-binding portion of the native ligand. A "native ligand" or "native binding partner" is defined herein as the molecule naturally produced by, for example, the animal or species which binds to the surface protein in nature. Preferably, the ligand moiety is a polypeptide or protein. As such, the native ligand of a cytokine receptor is the native cytokine. In another embodiment, the ligand moiety can comprise a binding fragment of an antibody, such as the variable region or a single chain antibody.

Preferably, the ligand moiety is a poly-peptide ligand to a cellular receptor. Examples of preferred ligands are growth factors, epidermal growth factor, vascular endothelial growth factors, interleukins, GM-CSF, G-CSF, M-CSF, EPO, TNF, interferons, and chemokines. Generally, the cellular receptor is not presented on the cell which expresses the viral receptor (e.g., a cell receptor which is bound by the virus during infection). In one embodiment, the cellular receptor which binds to the ligand moiety is not an Fc receptor. Thus, in this embodiment, the viral receptor-ligand fusion molecule is not an immunoadhesin.

The ligand moiety can have an amino acid sequence which is the same or substantially the same as an amino acid sequence of at least the receptor-binding portion of a native ligand for the cellular receptor. Similar to cellular receptors, many of the corresponding ligands have been identified, sequenced and characterized, including the portions thereof which bind to the receptor. The ligand moiety can, therefore, include the same or substantially the same sequence of the entire native ligand. Alternatively, ligand moiety comprises the receptor binding portion of the native ligand, eliminating, in some cases, the effector function of the ligand.

In another embodiment, the ligand moiety is selected or derived from native ligands or binding partners to a cellular surface molecule of the target cell. A "cellular surface molecule" as defined herein can be a peptide (including post-translationally modified proteins, such as amidated, demethylated, methylated, prenylated, palmitoylated, glycosylated, myristylated, acetylated or phosphorylated proteins), sugar, lipid, steriod, anion or cation, or a combination thereof which binds the ligand moiety.

The phrase "substantially the same sequence" is intended to include sequences which bind the surface protein and possess a high percentage of (e.g., at least about 90%, preferably at least about 95%) sequence identity with the native sequence. The modifications to the sequence can be conserved or non-conserved, natural and unnatural, amino acids and are preferably outside of the binding domain. Amino acids of the native sequence for substitution, deletion, or conservation can be identified, for example, by a sequence alignment between proteins from related species or other related proteins.

Where the ligand moiety comprises a binding fragment of an antibody, many antibodies to surface proteins are known or are commercially available, as are the amino acid sequences which are responsible for binding. Alternatively, novel antibodies can be prepared by methods known in the art, such as by Harlow and Lane, "Antibodies, A Laboratory Manual," Cold Spring Harbor Laboratory: Cold Spring Harbor, N.Y. (1988).

As set forth above, the soluble viral receptor moiety of the soluble viral receptor ligand fusion molecule, including soluble forms of the viral receptor, bind to a specified viral target on the virus (viral vector), generally a surface protein of the viral particle. In a preferred embodiment, the viral receptor moiety is a polypeptide which has an amino acid sequence which is the same or substantially the same as an amino acid sequence of at least the viral-binding portion of a native extracellular domain of a viral cellular receptor, such as the viral cellular receptor on a cell which is subject to infection by the viral vector. The viral surface protein is thus generally the viral protein which binds to this cell and activates or otherwise induces steps for viral entry and, thus, infection. Where the viral vector is a pseudotyped viral vector (such as where the vector is a retrovirus containing the envelope protein of another retrovirus, of an orthomyxovirus or of a rhabdovirus), as discussed above, it is understood that the viral cellular receptor generally corresponds to the env protein incorporated into the viral particle. In the case where the viral surface protein is an env protein, the viral receptor moiety generally binds the env SU protein and, thereby, activates the env TM protein, inducing or mediating virus-cell membrane fusion and viral entry. As such, a "viral cellular receptor" is a receptor molecule in or on a cell which binds to a natural or non-natural viral particle or protein, for example, in the course of infection. Non-natural viral particles include pseudotyped viruses, replication defective viruses, attenuated viruses, or recombinantly engineered viruses.

Examples of viral cellular receptors include the subgroup A avian leukosis virus receptor, the subgroup B and D avian leukosis virus receptor, the CD4 receptor for human and simian immunodeficiency viruses, the amphotropic and ecotropic murine leukemia virus receptors, the bovine leukemia virus receptor, the gibbon ape leukemia virus receptor, the poliovirus receptor, the major subgroup rhinovirus receptor (ICAM1), the adenovirus and coxsackie virus receptor (CAR), the coronavirus receptors (e.g. aminopeptidase N and MHVR), and sialic acid and other carbohydrate receptors (e.g., for orthomyxoviruses and paramyxoviruses). Many viral cellular receptors are known in the art, including the sequences thereof.

Cellular receptors are generally transmembrane proteins comprising intracellular, transmembrane (characterized by highly hydrophobic regions in the sequence) and extracellular domains. It is generally preferred that the viral receptor moiety comprises the native extracellular domain of the receptor molecule. As above with the ligand moiety, the viral receptor moiety can alternatively comprise the viral binding moiety of the extracellular domain of the receptor and mutations of the extracellular domain. The viral binding moiety can be identified or confirmed by manufacturing various fragments of the extracellular domain and screening them for their ability to bind. As above, viral-binding mutations to the extracellular domain can be manufactured as well. Mutations to the extracellular domain include conservative and non-conservative amino acid substitutions, particularly those not implicated in the binding of the viral particle. The phrase "substantially the same sequence" is intended to include sequences which bind the viral protein and possess a high percentage of (e.g., at least about 90%, preferably at least about 95%) amino acid sequence identity with the native sequence. The modifications to the sequence can be conserved or non-conserved amino acids.

The phrase "conservative amino acid substitutions" is intended to mean amino acids which possess similar side chains (e.g., hydrophobic, hydrophilic, aromatic, etc.), as is known in the art.

The viral receptor moiety can also be a sugar, lipid, steroid, nucleic acid, small molecule, anion or cation, or combination thereof which binds the specified viral target molecule. The binding can be via a covalent bond, ionic bonding, hydrogen bonding or other mechanism. One embodiment of the viral receptor moiety comprises an antigen-binding fragment of an antibody which recognizes and binds to the viral vector (virus). However, where one moiety of the soluble viral receptor-ligand fusion molecule comprises an antibody fragment, it is preferred that the other moiety does not comprise an antibody fragment.

The soluble viral receptor and ligand fusion moieties of the soluble viral receptor-ligand fusion molecule can be directly bonded together or through a linking moiety. Where one or both of the moieties are polypeptides, a peptide bond or peptide linker is preferred, thereby obtaining a "fusion protein" of the two moieties which can be expressed by a single nucleic acid construct in series. The two moieties can alternatively be linked directly or indirectly other than via a peptide bond or peptide linker, thereby obtaining a "conjugate".

Where the moieties are directly bonded to each other, the bond can be covalent, as in a peptide bond, ionic bonding or hydrogen bonding. Where the bond is a peptide bond, the first moiety can be bonded to the N-terminus of the second moiety via the C-terminus, or vice versa. It is acknowledged that one fusion protein may possess greater activity than a second fusion protein due to conformational or steric considerations.

Where one or more of the moieties are not poly-peptides, they can be joined via chemical reaction through functional groups present on each moiety which, under the appropriate conditions, will react with each other. For example, acid groups (or activated derivatives thereof) can be reacted with amines, alcohols or thiols to form amide or ester bonds, as is known in the art.

Alternatively, a linking moiety is employed to link the two moieties. The linker can preferably be a flexible linker and sufficient in length to separate the moieties in space, thereby not restricting the ability of the soluble viral receptor-ligand fusion molecule to bind independently and maintain the proper conformation. Again, where both moieties are polypeptides, the linker moiety will generally be a peptide, polypeptide, or a "pseudopeptide". A "pseudopeptide" is a bifunctional linker which contains at least one non-amino acid and reacts to form a peptide bond, or other bond, with the terminal amine or carboxyl group of the moiety. For example, a peptide characterized by substitution of the terminal amine for a carboxyl group can function to react with the amine terminus of each moiety. Such as linker is considered to be a "pseudopeptide." Similarly, a peptide characterized by substitution of the terminal carboxyl for an amine group can function to react with the carboxyl terminus of each moiety.

Generally, the linker will be a peptide linker which will link the amine terminus of one moiety to the carboxyl terminus of the second moiety. One advantage to such a molecule is the ability to express the fusion molecule as a fusion protein in a recombinant host cell with a single nucleic acid construct.

Preferred peptide linkers can be obtained from immunoglobulin hinge regions, such as a proline rich region. Also, linkers can be characterized by little steric hindrance, thereby permitting maximal independent movement of the two moieties, such as with a polyglycine linker. Alternatively, the linker selected to be reactive to or inert to cellular proteases can be desirable. In another embodiment, the linker can be selected to avoid or minimize an immune response against the fusion protein. The length of the linker also is not particularly critical. Typically, the length of the linker will be between about 2 and about 20 amino acids. As can be seen, the selection of the particular linking group is not critical to the invention.

In yet another embodiment, the linker can be a bifunctional compound which will react with other functional groups on the two binding moieties, such as in the reaction of acids and amines or alcohols (as present in peptides, carbohydrates and lipids, for example) in the formation of amides or esters.

A particular combination of the above soluble viral receptor and ligand moieties of the soluble viral receptor-ligand fusion molecule includes the selection of a polypeptide ligand to a cell-type specific cellular receptor linked, via a peptide linker through a terminus of the ligand to the terminus of at least the viral-binding moiety of the extracellular domain of a viral cellular receptor (or a mutant thereof, as defined above).

For example, the C-terminus of the ligand polypeptide is linked to the N-terminus of the viral receptor polypeptide via the polypeptide linker or the N-terminus of the ligand polypeptide is linked to the C-terminus of the viral receptor polypeptide via the polypeptide linker.

The soluble viral receptor-ligand molecules can be manufactured according to methods generally known in the art. For example, where one or both the viral receptor and ligand moieties is a nonpeptide, the fusion molecule can be manufactured employing known organic synthesis methods useful for reacting a functional or reactive group on one moiety with a functional or reactive group on the other moiety or, preferably, a linker. In carrying out the synthesis, derivation or inactivation of the functional group(s) required for binding to the moiety's binding partner should be avoided. Appropriate syntheses are highly dependent upon the chemical nature of the viral receptor and ligand moieties and, generally, can be selected from an advanced organic chemistry text, such as March, et al. *Advanced Organic Chemistry,* 3rd Edition, John E. Wiley & Sons, Inc.: New York, N.Y. (1985), or other known methods.

Where the viral receptor and ligand moieties are polypeptides, each moiety can be a conjugate or a fusion protein and manufactured according to known methods. Where a fusion protein is desired, the molecule can be manufactured according to known methods of recombinant DNA technology. For example, the fusion protein can be expressed by a nucleic acid molecule comprising sequences which code for both moieties, such as by a fusion gene.

Equivalents

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of targeting viral entry comprising combining:
    a) a target cell;
    b) a viral vector which has a targeting molecule which binds to a surface protein on said target cell; and
    c) a soluble viral receptor-ligand fusion molecule, wherein the soluble viral receptor moiety is an extracellular domain of a viral cellular receptor or a functional derivative thereof and the ligand moiety binds to a cell-type specific cellular receptor wherein viral entry is targeted.

2. The method of claim 1 wherein the viral vector is a retroviral vector.

3. The method of claim 1 wherein the viral vector encodes a heterologous therapeutic protein.

4. The method of claim 3 wherein the therapeutic protein is selected from the group consisting of: immunogens, cytokines, tumor necrosis factor, interferons, interleukins, adenosine deaminase, insulin, T-cell receptors, soluble CD4, epidermal growth factor, human growth factor, blood factors, such as Factor VIII, Factor IX, cytochrome b, glucocerebrosidase, ApoE, ApoC, ApoAI, the LDL receptor, negative selection markers, anti-angiogenic factors, Fc receptors, plasminogen activators, dopamine, MHC, tumor suppressor genes, monoclonal antibodies or antigen binding fragments thereof, drug resistance genes, ion channels and adrenergic receptors.

5. A method of targeting viral entry comprising combining:
    a) a target cell; b) a viral vector which has a targeting molecule which binds to a surface protein on said target cell; and
    c) a soluble viral receptor, wherein the soluble viral receptor is an extracellular domain of a viral cellular receptor or a functional derivative thereof wherein viral entry is targeted.

6. The method of claim 5 wherein the viral vector is a retroviral vector.

7. The method of claim 5 wherein the viral vector encodes a heterologous therapeutic protein.

8. The method of claim 7 wherein the therapeutic protein is selected from the group consisting of: immunogens, cytokines, tumor necrosis factor, interferons, interleukins, adenosine deaminase, insulin, T-cell receptors, soluble CD4, epidermal growth factor, human growth factor, blood factors, such as Factor VIII, Factor IX, cytochrome b, glucocerebrosidase, ApoE, ApoC, ApoAI, the LDL receptor, negative selection markers, anti-angiogenic factors, Fc receptors, plasminogen activators, dopamine, MHC, tumor suppressor genes, monoclonal antibodies or antigen binding fragments thereof, drug resistance genes, ion channels and adrenergic receptors.

9. A method for delivering a viral vector to a cell comprising contacting a target cell with:
    a) a viral vector which has a targeting molecule which binds to a surface protein on said target cell; and
    b) a soluble viral receptor-ligand fusion molecule, wherein the soluble viral receptor moiety is an extracellular domain of a viral cellular receptor or a functional derivative thereof and the ligand moiety binds to a cell-type specific cellular receptor wherein a viral vector is delivered to a cell.

10. The method of claim 9 wherein the viral vector is a retroviral vector.

11. The method of claim 10 wherein the viral vector encodes a heterologous therapeutic protein.

12. The method of claim 11 wherein the therapeutic protein is selected from the group consisting of: immunogens, cytokines, tumor necrosis factor, interferons, interleukins, adenosine deaminase, insulin, T-cell receptors, soluble CD4, epidermal growth factor, human growth factor, blood factors, such as Factor VIII, Factor IX, cytochrome b, glucocerebrosidase, ApoE, ApoC, ApoAI, the LDL receptor, negative selection markers, anti-angiogenic factors, Fc receptors, plasminogen activators, dopamine, MHC, tumor suppressor genes, monoclonal antibodies or antigen binding fragments thereof, drug resistance genes, ion channels and adrenergic receptors.

13. A method for delivering a viral vector to a cell comprising contacting a target cell with:
    a) a viral vector which has a targeting molecule which binds to a surface protein on said target cell; and
    b) a soluble viral receptor, wherein the soluble viral receptor is an extracellular domain of a viral cellular receptor or a functional derivative thereof wherein a viral vector is delivered to a cell.

14. The method of claim 13 wherein the viral vector is a retroviral vector.

15. The method of claim 13 wherein the viral vector encodes a heterologous therapeutic protein.

16. The method of claim 15 wherein the therapeutic protein is selected from the group consisting of: immunogens, cytokines, tumor necrosis factor, interferons, interleukins, adenosine deaminase, insulin, T-cell receptors, soluble CD4, epidermal growth factor, human growth factor, blood factors, such as Factor VIII, Factor IX, cytochrome b, glucocerebrosidase, ApoE, ApoC, ApoAI, the LDL receptor, negative selection markers, anti-angiogenic factors, Fc receptors, plasminogen activators, dopamine, MHC, tumor suppressor genes, monoclonal antibodies or antigen binding fragments thereof, drug resistance genes, ion channels and adrenergic receptors.

17. A method of targeting retroviral entry comprising combining:
    a) a target cell;
    b) a retroviral vector which has a targeting molecule which binds to a surface protein on said target cell; and
    c) a soluble retroviral receptor-ligand fusion molecule, wherein the soluble retroviral receptor moiety is an extracellular domain of a retroviral cellular receptor or a functional derivative thereof and the ligand moiety binds to a cell-type specific cellular receptor wherein retroviral entry is targeted.

18. The method of claim 17 wherein the retroviral vector is avian leukosis virus and the soluble retroviral cellular receptor moiety is selected from the group consisting of a soluble subgroup A avian leukosis virus receptor and a soluble subgroup B avian leukosis virus receptor.

19. The method of claim 17 wherein the retroviral vector encodes a heterologous therapeutic protein.

20. A method of targeting retroviral entry comprising combining:
   a) a target cell;
   b) a retroviral vector which has a targeting molecule which binds to a surface protein on said target cell; and
   c) a soluble retroviral receptor, wherein the soluble retroviral receptor is an extracellular domain of a retroviral cellular receptor or a functional derivative thereof wherein retroviral entry is targeted.

21. The method of claim 20 wherein the retroviral vector is avian leukosis virus and the soluble retroviral receptor is selected from the group consisting of a soluble subgroup A avian leukosis virus receptor and a soluble subgroup B avian leukosis virus receptor.

22. The method of claim 20 wherein the retroviral vector encodes a heterologous therapeutic protein.

23. A method for delivering a retroviral vector to a cell comprising contacting a target cell with:
   a) a retroviral vector which has a targeting molecule which binds to a surface protein on said target cell; and
   b) a soluble retroviral receptor-ligand fusion molecule, wherein the soluble retroviral moiety is an extracellular domain of a retroviral cellular receptor or a functional derivative thereof and the ligand moiety binds to a cell-type specific cellular receptor wherein a retrovirus is delivered to a cell.

24. The method of claim 23 wherein the retroviral vector is avian leukosis virus and the soluble retroviral cellular receptor moiety is selected from the group consisting of a soluble subgroup A avian leukosis virus receptor and a soluble subgroup B avian leukosis virus receptor.

25. The method of claim 23 wherein the retroviral vector encodes a heterologous therapeutic protein.

26. A method for delivering a retroviral vector to a cell comprising contacting a target cell with:
   a) a retroviral vector which has a targeting molecule which binds to a surface protein on said target cell; and
   b) a soluble retroviral receptor, wherein the soluble retroviral receptor is an extracellular domain of a retroviral cellular receptor or a functional derivative thereof wherein the retrovirus is delivered to a cell.

27. The method of claim 26 wherein the retroviral vector is avian leukosis virus and the soluble retroviral receptor is selected from the group consisting of a soluble subgroup A avian leukosis virus receptor and a soluble subgroup B avian leukosis virus receptor.

28. The method of claim 26 wherein the retroviral vector encodes a heterologous therapeutic protein.

\* \* \* \* \*